United States Patent [19]
Paret et al.

[11] 4,009,084
[45] Feb. 22, 1977

[54] PROCESS FOR THE SEPARATION OF DIOLEFINS FROM MIXTURES CONTAINING THE SAME

[75] Inventors: Giancarlo Paret, Milan; Ermanno Cinelli, San Donato Milanese, both of Italy

[73] Assignee: Sham Progetti S.p.A., Milan, Italy

[22] Filed: Jan. 15, 1975

[21] Appl. No.: 541,343

Related U.S. Application Data

[63] Continuation of Ser. No. 305,549, Nov. 10, 1972, abandoned, which is a continuation of Ser. No. 55,660, July 17, 1970, abandoned.

[30] Foreign Application Priority Data

July 18, 1969 Italy .................................. 19814/69

[52] U.S. Cl. .................................. 203/53; 203/58; 208/326; 260/681.5 R
[51] Int. Cl.$^2$ .......................................... B01D 3/34
[58] Field of Search .................. 203/58, 60, 62, 63, 203/53; 260/681.5 R, 681.5 C, 677 A; 208/326

[56] References Cited

UNITED STATES PATENTS

| | | | |
|---|---|---|---|
| 3,050,573 | 8/1962 | Anderson et al. | 260/681.5 R |
| 3,201,492 | 8/1965 | Sherk | 260/681.5 R |
| 3,434,936 | 3/1969 | Luther et al. | 203/58 |
| 3,795,588 | 3/1974 | Preusser et al. | 203/58 |

*Primary Examiner*—Frank W. Lutter
*Assistant Examiner*—Frank Sever
*Attorney, Agent, or Firm*—Ralph M. Watson

[57] ABSTRACT

A multi-stage process for the solvent extraction of butadiene from a mixed feed stock containing butadiene, C-4 saturated and olefinic hydrocarbons and acetylenic compounds is disclosed wherein the feed stock is contacted with N-formyl morpholine and C-4 saturated and olefinic hydrocarbons are separated therefrom in a first stage and, in a second stage, the solvent and acetylenic compounds present in the feed stock are respectively separated from one another.

1 Claim, 3 Drawing Figures

PROCESS FOR THE SEPARATION OF DIOLEFINS FROM MIXTURES CONTAINING THE SAME

This is a continuation of application Ser. No. 305,549, filed Nov. 10, 1972, now abandoned, which was a continuation of application Ser. No. 55,660, filed July 17, 1970, now abandoned.

This invention relates to a process for separating conjugated diolefins from mixtures in which they are contained.

More particularly this invention relates to the extraction of butadiene and isoprene from mixtures containing them.

It is known that conjugated diolefins have assumed an ever-growing importance in the industrial field owing to the possibilities, offered by the techniques, of producing stereospecific polymers substitutive of the natural rubber.

It is also known that diolefin monomers must be of well defined purity when used for producing stereospecific polymers because they have to be free from all the components which adversely affect catalyst activity.

It is also known that the above mentioned diolefins may be prepared in different ways and that according to their preparation the composition of the mixture, from which they are separated, is different; said ways are substantially two:
  dehydrogenation of olefin compounds to dienes
  chemical synthesis processes which use carbonyl compounds.

In the first case together with the diene, also olefin hydrocarbons are also obtained which have substantially the same number of carbon atoms, while in the second case carboxylic compounds such as aldehydes and ketones are present.

We have found a simple and economical process, and this is the subject of the present invention, suitable for the separation of diolefins from mixtures in which they are contained.

According to the above mentioned process oxygenated morpholine derivatives are used as extraction and extractive distillation agents. The above mentioned oxygenated morpholine derivatives are preferably used in an aqueous mixture.

The oxygenated morpholine derivatives advantageously used are all the ones having an oxygenated substitute on the morpholine ring. Particularly the following ones can be mentioned as examples: N-formyl-morpholine, 2-formyl-morpholine, 3-formyl-morpholine, morpholine-acetone and the like.

The solvent, giving the best results, is N-formyl-morpholine, which hereinafter will be simply called formyl-morpholine.

In fact, we have found that under particular conditions formyl-morpholine is a very good solvent, selective for diene hydrocarbons. By using formyl-morpholine in the process for separating diene hydrocarbons there are many advantages as over conventional solvents both from the technical and economical point of view.

In fact formyl-morpholine can be simply produced from easily available and cheap materials. Besides, formyl-morpholine has a greater selectivity for diolefines than for more polar compounds such as, for instance, cyclodiolefines, carbonyl and acetylene compounds; in such a way said compounds can be simply removed from the desired diolefine. Formyl-morpholine is preferably used as an aqueous mixture.

Mixtures containing from 0 to 20% by weight water and from 80 to 100% by weight morpholine have been particularly effective.

In the case of a low boiling diolefine separation, it is advantageous to work under a certain pressure so that throughout the whole cycle temperatures below room temperature are not necessary.

The process of the present invention may be utilized for obtaining dienes such as butadiene, isoprene, piperylene, cyclopentadiene, 1-3 hexadiene, 2-4 hexadiene, 2-methyl-pentadiene 1,3; 3-methyl-pentadiene 1,3; 1,3 dimethyl-butadiene 1,3; 2,3 dimethyl-butadiene 1,3; 2-ethyl-butadiene 1,3; methyl cyclopentadiene; 2,3 dimethylcyclopentadiene, cyclohexadiene 1,3 and the like.

Our invention will now be explained by the following particular illustrative examples, reference being made to the enclosed drawings which illustrate diagramatically some dispositions of apparatus by which the invention can be put into practice.

Figure 1:
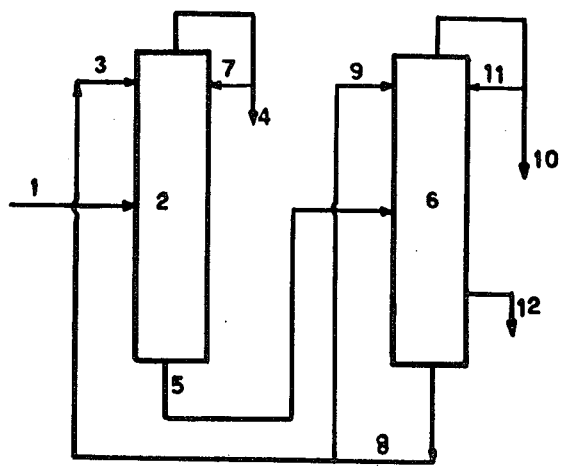
FIG. 1 shows a process scheme for separating conjugated diolefines from mixtures containing them together with other hydrocarbons and oxygenated compounds.

In FIG. 1 the feed containing diolefines enters the column 2 through line 1. In the same column 2 the solvent, which is a mixture of formyl-morpholine and water, enters through 3.

Monoolefines and saturated compounds, which are partially recycled into the column through 7, leave the top of the first column through line 4. A mixture comprising the solvent, diolefines and more polar compounds, such as acetylenic and possibly oxygenated compounds, leave, through line 5, the bottom of the column 2. Said mixture is fed to the column 6, to the top of which the solvent is fed through line 9.

The conjugated acyclic diolefines leave the top of column 6 through line 10 and are partially recycled to the column through line 11. The more polar compounds such as cyclic conjugated diolefines and acetylenic and carbonyl compounds leave the column through 12, while the lean solvent, leaving the bottom through line 8, is recycled to the columns 2 and 6 through lines 3 and 9.

EXAMPLE 1

A feed having the following composition:

| | | |
|---|---|---|
| Isoprene | 96.99 % by weight | |
| 2MB 1 | 1 % by weight | (2MB 1 = 2 methyl-butene 1) |
| 2MB 2 | 1 % by weight | (2MB 2 = 2 methyl-butene 2) |
| Acetone | 1 % by weight | |

| Isopropenyl-acetylene | 0.01 % by weight | was treated in a cycle such as the one shown in FIG. 1, composed of two glass columns having 44 plates each.

The feed was introduced in the vapour phase to the 22nd plate of the first column; the aqueous solvent (6&% weight $H_2O$) was fed to the top plate in a ratio of 20 to 1 by weight referred to the feed; the reflux ratio at the column top was 40/1.

The second column was like the first; the rich solvent leaving the bottom of the first column was fed to the 22nd plate of the second column; aqueous solvent (6% $H_2O$) in the ratio 4/1 referred to the feed of the plant was introduced at the column top; the reflux ratio in the second column was 0.8/1.

The first column overhead product has the following composition:

| Isoprene | 51 % by weight |
| 2MB 1 | 25 % by weight |
| 2MB 2 | 25 % by weight |
| Water | not determined |

The second column gave an overhead product of this composition:

| Isoprene | 99.95 % by weight |
| 2MB 2 | 0.05 % by weight |
| Acetone | — |
| Isopropenyl-acetylene | 15 p.p.m. |
| Water | not determined |

The side stream leaving the column from a point near the bottom had the following composition:

| Isoprene | 29.4 % by weight |
| Acetone | 70 % by weight |
| Isopropenyl-acetylene | 0.6 % by weight |
| $H_2O$ | not determined |

Altogether, there was 97.7 of the fed isoprene with a 99.9% purity.

The obtained product, after dehydration, is polymerizable without limitation.

EXAMPLE 2

We used a cycle like the one shown in FIG. 1 but the columns worked at a pressure of about 3 kg/cm². The feed was constituted of a hydrocarbon mixture produced by steam cracking; it contained:

| saturated hydrocarbons | $C_4$ | 20 % by weight |
| olefinic hydrocarbons | $C_4$ | 45 % by weight |
| butadiene | | 35 % by weight |
| acetylenic compounds | | 1000 p.p.m. | and it was fed at a rate of 1 kg/h to the column 1 through line 1.

Aqueous formyl-morpholine, having 10% by weight $H_2O$, was fed through line 3 at a rate of 15 kg/h.

By working with a reflux ratio 1/1, we obtained, through 4, 0.65 kg/h of a fraction containing substantially saturated hydrocarbons and olefines, practically butadiene-free.

A mixture of solvent, diolefines and acetylenic compounds left the column bottom through line 5; said mixture was fed to the column 6, from which, with the reflux ratio still 1/1, 0.345 kg/h of butadiene with 99.5% purity and less than 30 p.p.m. of acetylenic compounds were obtained as overhead product. The side stream 12 is butadiene containing substantially all the fed acetylenic compounds at a rate of 5 gr/h.

The solvent was recovered from the column bottom and then recycled.

EXAMPLE 3

Figure 2:
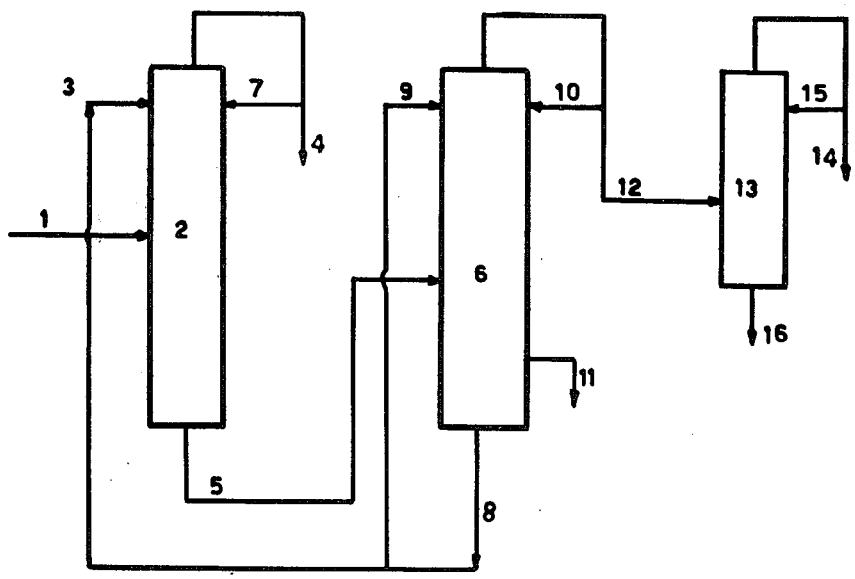
FIG. 2 shows a process scheme for separating particular diolefines when conjugated isomeric diolefines are also present in the mixture.

A cycle like the one shown in the FIG. 2 was used for obtaining isoprene from a hydrocarbon mixture coming from an amylenes dehydrogenation plant.

The feed had the following composition:

| Isoprene | 15 % by weight |
| Olefines $C_5$ | 30 % by weight |
| Saturated hydrocarbons $C_5$ | 53 % by weight |
| Piperylene | 2 % by weight |
| Acetylenic compounds and cyclopentadiene | 1000 p.p.m. |

The feed was introduced through line 1 into the column 2 at a rate of 1 kg/h.

The solvent (aqueous formyl-morpholine with 5% $H_2O$) was fed through line 3 to the column top at a rate of 25 kg/h.

By working with a reflux ratio of 1.2/1, 0.83 kg/h of a mixture containing substantially all saturated hydrocarbons and olefines, practically diolefine-free was obtained through 4; said mixture was partially recycled into the column through 7. From the bottom, through line 5, a mixture of solvent, conjugated diolefines and more polar compounds (acetylenic compounds and cyclopentadiene) was obtained. Said mixture was fed to the column 6 wherefrom, with the reflux ratio 1/1, a mixture containing about 6% by weight piperylene at a rate 0.16 kg/h was obtained as overhead product, the remaining part of the mixture being substantially isoprene containing less than 30 p.p.m. of acetylenic compounds and less than 3 p.p.m. of cyclopentadiene.

The side stream 11 was a mixture containing piperylene and more polar compounds in which cyclopentadiene prevailed; the mixture rate was 0.01 kg/h.

From the bottom of the column lean solvent was obtained through line 8; said solvent through lines 3 and 9 is recycled to columns 2 and 6. The diolefines mixture, which in part was recycled to the column 6 through 10, was fed through line 12 to the rectification column 13. By means of a reflux ratio of 8/1 we obtained, through 14, 0.15 kg/h of isoprene with a 99.99% purity, containing less than 3 p.p.m. cyclopentadiene.

From the bottom of the column 13 we obtained through line 16 substantially pure piperylene.

EXAMPLE 4

Figure 3:
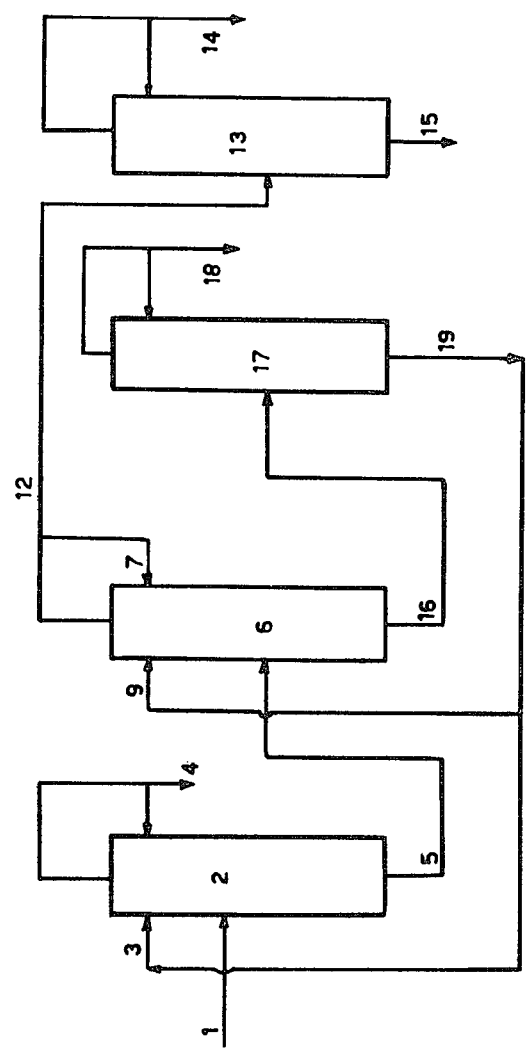
FIG. 3 shows a process scheme utilized for obtaining isoprene from mixtures containing high amounts of more polar compounds such as cyclic diolefines, acetylenic and oxygenated compounds.

A working cycle was used which was like the one shown in FIG. 3. Isoprene and piperylene were recovered from hydrocarbon mixtures coming from a stream cracking plant.

The feed composition was the following one:

| | |
|---|---|
| Isoprene | 10 % by weight |
| Piperylene | 5 % by weight |
| Cyclopentadiene | 10 % by weight |
| Saturated hydrocarbons $C_5$ | 45 % by weight |
| Olefines $C_5$ | 30 % by weight |

The feed was introduced into the column 2 through line 1 at a rate of 1 kg/h while the solvent (formyl-morpholine with 5% water) was introduced into the same column through line 3 at a rate of 20 kg/h. By working with a reflux ratio 1/1, 0.75 kg/h of a mixture of saturated hydrocarbons and olefines, substantially diolefine-free, were obtained from outlet 4.

From the bottom, through line 5, a mixture of solvent, acyclic conjugated diolefine and cyclopentadiene was obtained; said mixture was fed into the column 6, from which, with the reflux ratio 1/1, as overhead product a mixture (0.12 kg/h) of isoprene and piperylene (83.3% isoprene and 16.7% piperylene) was obtained. Said mixture flows out through line 12 and is treated as in preceding example; so that as overhead product 0.10 kg/h of isoprene with a 99.99% purity and as bottom product 0.02 kg/h of piperylene with a 99.9% purity were obtained.

The bottom product of the column 6 was fed, by means of line 16, to the column 17 in which, with the reflux ratio 0.1/1, 0.13 kg/h of a mixture of cyclopentadiene and piperylene (77% cyclopentadiene and 23% piperylene) were obtained through outlet 18, as overhead product.

From the bottom of the column 17 lean solvent, which is recycled as described, was obtained.

What we claim is:

1. An extractive distillation process for separating butadiene from a hydrocarbon mixture containing butadiene, C-4 saturated and olefinic hydrocarbons and acetylenic compounds which comprises the steps of feeding said hydrocarbon mixture to a first stage extractive distillation column at a point spaced below the top thereof and feeding an extractive distillation agent consisting of an aqueous mixture of N-formyl morpholine and up to 20% of water to said first stage extractive distillation column at the top thereof, withdrawing said C-4 saturated and olefinic hydrocarbons from the top of the first stage extractive distillation column, withdrawing the butadiene, the extractive distillation agent and the acetylenic compounds as a bottom product from said first stage extractive distillation column, thereafter feeding said bottom product to a second stage extractive distillation column at a point spaced below the top thereof, recovering butadiene from said second stage extractive distillation column as overhead, recovering the acetylenic compounds and the extractive distillation agent from the bottom of the second stage extractive distillation column, dividing the extractive distillation agent recovered from the bottom of the second stage extractive distillation column into two portions, recycling one of said portions to the first stage extractive distillation column to the top thereof, and recycling the other of said portions to said second stage extractive distillation column to the top thereof.

* * * * *

UNITED STATES PATENT AND TRADEMARK OFFICE
CERTIFICATE OF CORRECTION

PATENT NO. : 4,009,084
DATED : February 22, 1977
INVENTOR(S) : Giancarlo Paret and Ermanno Cinelli It is certified that error appears in the above-identified patent and that said Letters Patent are hereby corrected as shown below:

First page, item "[54]", Correct the title to read --PROCESS FOR THE SEPARATION OF BUTADIENE FROM MIXTURES CONTAINING THE SAME--.

First page, item "[73]", Correct the line to read --Assignee: Snamprogetti S.p.A., Milan, Italy--.

First page, item "[63]", Correct "Ser.No. 305,549" to read --Ser. No. 305,469--.

Column 1, lines 1 & 2, Correct the title to read --PROCESS FOR THE SEPARATION OF BUTADIENE FROM MIXTURES CONTAINING THE SAME--.

line 5, Correct "305,549" to read --305,469--.

UNITED STATES PATENT AND TRADEMARK OFFICE
CERTIFICATE OF CORRECTION

PATENT NO. : 4,009,084
DATED : February 22, 1977
INVENTOR(S) : Giancarlo Paret and Ermanno Cinelli It is certified that error appears in the above–identified patent and that said Letters Patent are hereby corrected as shown below:

Column 3, line 9, After "(6" delete "&".

line 10, Before "weight" insert --by--.

line 46, After "was" insert --recovered:--.

Signed and Sealed this sixteenth Day of August 1977

[SEAL]

Attest:

RUTH C. MASON
*Attesting Officer*

C. MARSHALL DANN
*Commissioner of Patents and Trademarks*